(12) United States Patent
Biyani (10) Patent No.: US 8,197,516 B2
(45) Date of Patent: Jun. 12, 2012

(54) LATERAL FIXATION ASSEMBLY FOR SPINAL COLUMN

(75) Inventor: Ashok Biyani, Sylvania, OH (US)

(73) Assignee: The University of Toledo, Toledo, OH (US)

(*) Notice: Subject to any disclaimer, the term of this patent is extended or adjusted under 35 U.S.C. 154(b) by 201 days.

(21) Appl. No.: 12/496,202

(22) Filed: Jul. 1, 2009

(65) Prior Publication Data

US 2010/0004689 A1    Jan. 7, 2010

Related U.S. Application Data

(60) Provisional application No. 61/077,260, filed on Jul. 1, 2008.

(51) Int. Cl.
*A61B 17/70* (2006.01)
(52) U.S. Cl. .......................... 606/250; 606/251; 606/258
(58) Field of Classification Search .............. 606/53–60, 606/246–279
See application file for complete search history.

(56) References Cited

U.S. PATENT DOCUMENTS

| | | | | |
|---|---|---|---|---|
| 7,175,622 B2* | 2/2007 | Farris | ............................ | 606/250 |
| 7,922,746 B2* | 4/2011 | Miller | ............................ | 606/258 |
| 7,927,357 B2* | 4/2011 | Sacher et al. | ................. | 606/258 |
| 7,942,907 B2* | 5/2011 | Richelsoph | ................... | 606/257 |
| 7,942,908 B2* | 5/2011 | Sacher et al. | ................. | 606/258 |
| 8,043,340 B1* | 10/2011 | Law | .............................. | 606/257 |
| 2003/0055427 A1* | 3/2003 | Graf | ................................ | 606/61 |
| 2005/0228378 A1* | 10/2005 | Kalfas et al. | .................... | 606/61 |
| 2005/0261685 A1* | 11/2005 | Fortin et al. | ...................... | 606/61 |
| 2006/0195087 A1* | 8/2006 | Sacher et al. | .................... | 606/61 |
| 2006/0195088 A1* | 8/2006 | Sacher et al. | .................... | 606/61 |
| 2006/0241591 A1* | 10/2006 | Biscup et al. | .................. | 606/60 |
| 2008/0021451 A1* | 1/2008 | Coull et al. | ..................... | 606/54 |
| 2008/0039843 A1* | 2/2008 | Abdou | ............................. | 606/61 |
| 2008/0215095 A1* | 9/2008 | Biedermann et al. | ......... | 606/246 |
| 2008/0234743 A1* | 9/2008 | Marik | ............................ | 606/257 |
| 2009/0204156 A1* | 8/2009 | McClintock et al. | ......... | 606/278 |
| 2010/0004689 A1 | 1/2010 | Biyani | | |
| 2010/0274288 A1* | 10/2010 | Prevost et al. | ................. | 606/257 |

OTHER PUBLICATIONS

Synthes Spine, Synex(tm) System Technique Guide, 2001.
Stryker, Thor(tm) Tumor Trauma Plate Operative Technique, 2008.

* cited by examiner

*Primary Examiner* — Eduardo C Robert
*Assistant Examiner* — Christina Negrelli
(74) *Attorney, Agent, or Firm* — MacMillan, Sobanski & Todd, LLC (57) ABSTRACT

A lateral fixation assembly engages vertebrae in a spinal column. The lateral fixation assembly includes a housing having a first rod and a second rod supported thereon. The first rod is adapted to be secured to a first vertebra in the spinal column and is fixed in position relative to the housing. The second rod is adapted to be secured to a second vertebra in the spinal column and is movable relative to the housing. Respective pluralities of such first and second rods may be provided. Staples having varying thicknesses may be provided to facilitate the installation of the lateral fixation assembly on the vertebrae in the spinal column. A temporary blocking device can be used to prevent relative movement of the movable rod during the installation of the lateral fixation assembly.

18 Claims, 9 Drawing Sheets

LATERAL FIXATION ASSEMBLY FOR SPINAL COLUMN

CROSS-REFERENCE TO RELATED APPLICATIONS

This application claims the benefit of U.S. Provisional Application No. 61/077,260 filed Jul. 1, 2008, the disclosure of which is incorporated herein by reference.

BACKGROUND OF THE INVENTION

This invention relates in general to the field of orthopedic surgery and more particularly to the area of spinal surgery. In particular, this invention relates to an improved structure for a lateral fixation assembly that is adapted to be installed during a spinal surgery to engage two more spinal vertebrae so as to maintain a desired spacing and alignment therebetween.

One example of a spinal surgery is referred to as a corpectomy, which is a procedure that involves the removal of one or more damaged vertebrae. Vertebrae can be damaged by a variety of causes including, but not limited to severe trauma and/or tumors. During a corpectomy procedure, the damaged vertebrae are removed and a replacement structure (such as a cage, for example) can be inserted into the corpectomy defect to restore the anterior column of the spine. Additionally, the replacement structure can be supplemented with other structures, such as for example a lateral fixation assembly. A lateral fixation assembly can be positioned to the side of the corpectomy defect and configured to provide support to the affected spinal region.

Known lateral fixation assemblies are fixed in a vertical direction and do not allow for vertical translation of the lateral fixation assembly. Thus, there is a need for a lateral fixation assembly that allows for vertical translation.

SUMMARY OF THE INVENTION

This invention relates to a lateral fixation assembly for supporting a spinal column. The lateral fixation assembly includes a housing assembly and a plurality of fixed rods connected to one end of the housing assembly. A plurality of movable rods is connected to the end of the housing assembly opposite the plurality of fixed rods. The movable rods have a major axis. The position of the movable rods can vary in a direction along the major axis of the movable rods between a first extended position and a second compressed position.

According to this invention, there is also provided a lateral fixation assembly for attachment to spinal vertebrae positioned above and below a corpectomy defect. The lateral fixation assembly includes a plurality of cleats configured for attachment to vertebrae and a plurality of anchors configured for insertion into the vertebrae and further configured for seating against the cleats. A plurality of fixed rods is attached to the anchors in one of the vertebrae. A plurality of movable rods is attached to the anchors of the other vertebrae, the movable rods having a major axis. A housing assembly is connected to and positioned between the fixed rods and the movable rods. The position of the movable rods can vary in a direction along the major axis of the movable rods between a first extended position and a second compressed position.

According to this invention, there is also provided a method of installing a lateral fixation assembly configured for attachment to spinal vertebrae positioned above and below a corpectomy defect. The method includes the steps of attaching a plurality of cleats to vertebrae located above and below the corpectomy defect, inserting a plurality of anchors through the cleats and into vertebrae, seating the anchors against the cleats, attaching a plurality of fixed rods to the anchors of one of the vertebrae, attaching a plurality of movable rods to the anchors of the other vertebrae, the movable rods having a major axes, the fixed rods and the movable rods connected to and positioned on opposite sides of a housing assembly, the movable rods initially in an extended position and releasing the movable rods from the initial extended position. The position of the movable rods can vary in a direction along the major axes between a first extended position and a second compressed position.

Various aspects of this invention will become apparent to those skilled in the art from the following detailed description of the preferred embodiments, when read in light of the accompanying drawings.

DETAILED DESCRIPTION OF THE PREFERRED EMBODIMENTS

Figure 1:
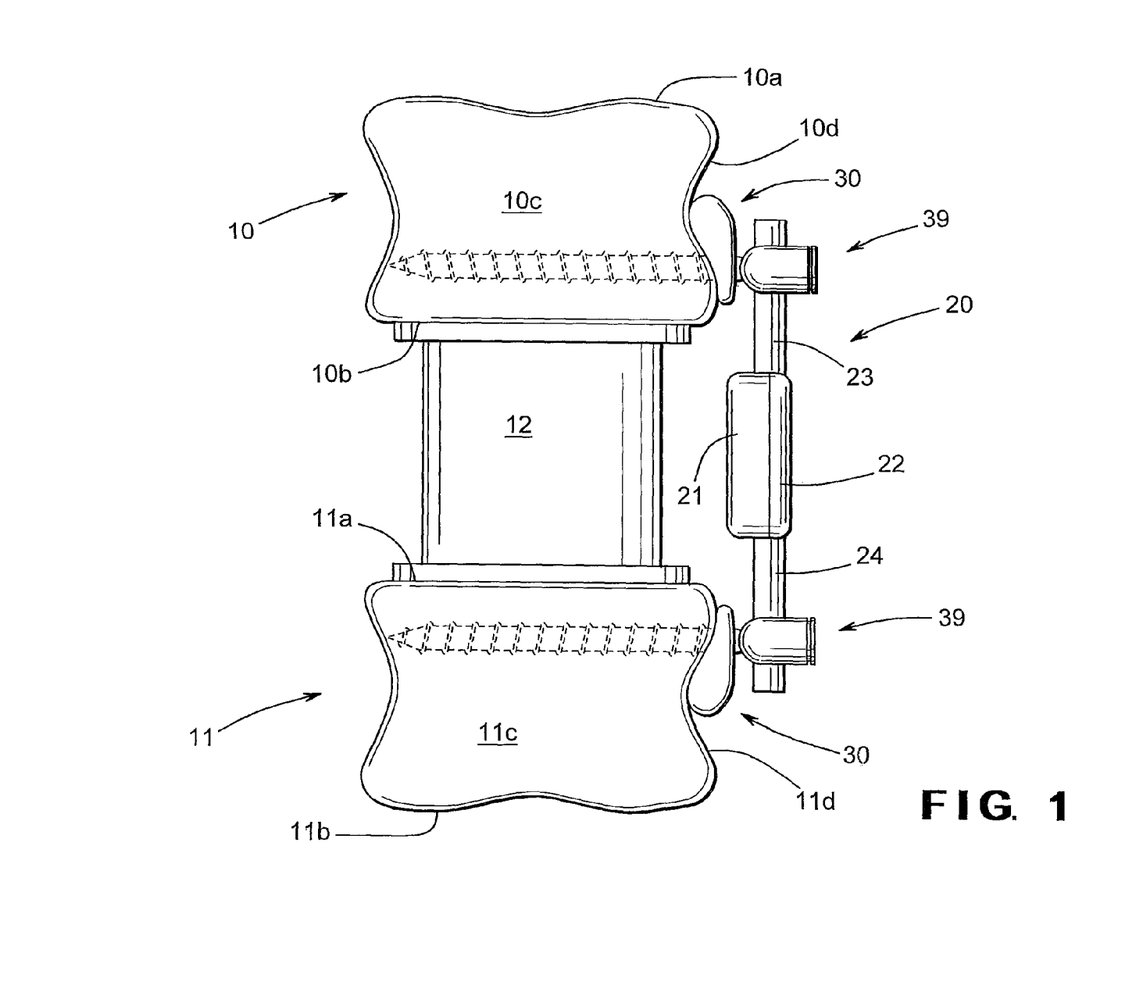
FIG. 1 is a side elevational view of a first embodiment of a lateral fixation assembly in accordance with this invention, shown installed on a pair of vertebrae in a spinal column.

Referring now to the drawings, there is illustrated in FIG. 1 a pair of vertebrae, indicated generally at 10 and 11, that form a portion of a human spinal column. In the illustrated embodiment, the vertebrae 10 and 11 are located in the lumbar region of the spinal column. However, the vertebrae 10 and 11 can be located in other regions of the spinal column.

As shown in FIG. 1, the upper vertebra 10 includes an upper end plate 10a, a lower end plate 10b, and a body 10c that extends between the upper end plate 10a and the lower end plate 10b. The body 10c of the first vertebra 10 includes a concavely-shaped waist region 10d that is located between the upper end plate 10a and the lower end plate 10b. Similarly, the lower vertebra 11 includes an upper end plate 11a, a lower end plate 11b, and a body 11c that extends between the upper end plate 11a and the lower end plate 11b. The body 11c of the vertebra 11 includes a concavely-shaped waist region 11d that is located between the upper end plate 11a and the lower end plate 11b. The vertebrae 10 and 11 define respective widths that can vary in accordance with the region of the spinal column in which the vertebrae 10 and 11 are located.

In the illustrated embodiment, the vertebrae 10 and 11 are separated by a defect region, which may be a corpectomy defect. The defect region may be formed during a surgical procedure when one or more damaged vertebrae (not shown) and adjacent fibro-cartilaginous structures commonly referred to as "discs" (not shown) are removed from the spinal column. As shown in FIG. 1, a replacement structure 12 can be inserted into the defect region, extending between the lower end plate 10b of the upper vertebra 10 and the upper end plate 11a of the lower vertebra 11. The replacement structure 12 is adapted to maintain a desired spacing and alignment between the vertebrae 10 and 11. The replacement structure 12 may be embodied as any structure that is suitable to restore and maintain the desired height within the defect region. In some embodiments, the replacement structure 12 can be packed with bone graft to facilitate fusion with the vertebrae 10 and 11. While the embodiment shown in FIG. 1 illustrates a single replacement structure 12, it should be understood that more than one replacement structure 12 can be used in the defect region.

A first embodiment of a lateral fixation assembly, indicated generally at 20, in accordance with this invention is secured to each of the vertebrae 10 and 11 and spans the defect region therebetween. The lateral fixation assembly 20 is adapted to supplement the support to the spinal column provided by the replacement structure 12, while allowing a limited amount of compression of the defect region after the lateral fixation assembly 20 has been installed. Such compression (which is manifested as a shortening of the distance between the lower end plate 10b of the upper vertebra 10 and the upper end plate 11a of the lower vertebra 11) can occur following the installation of the replacement structure 12.

Figures 2, 3:
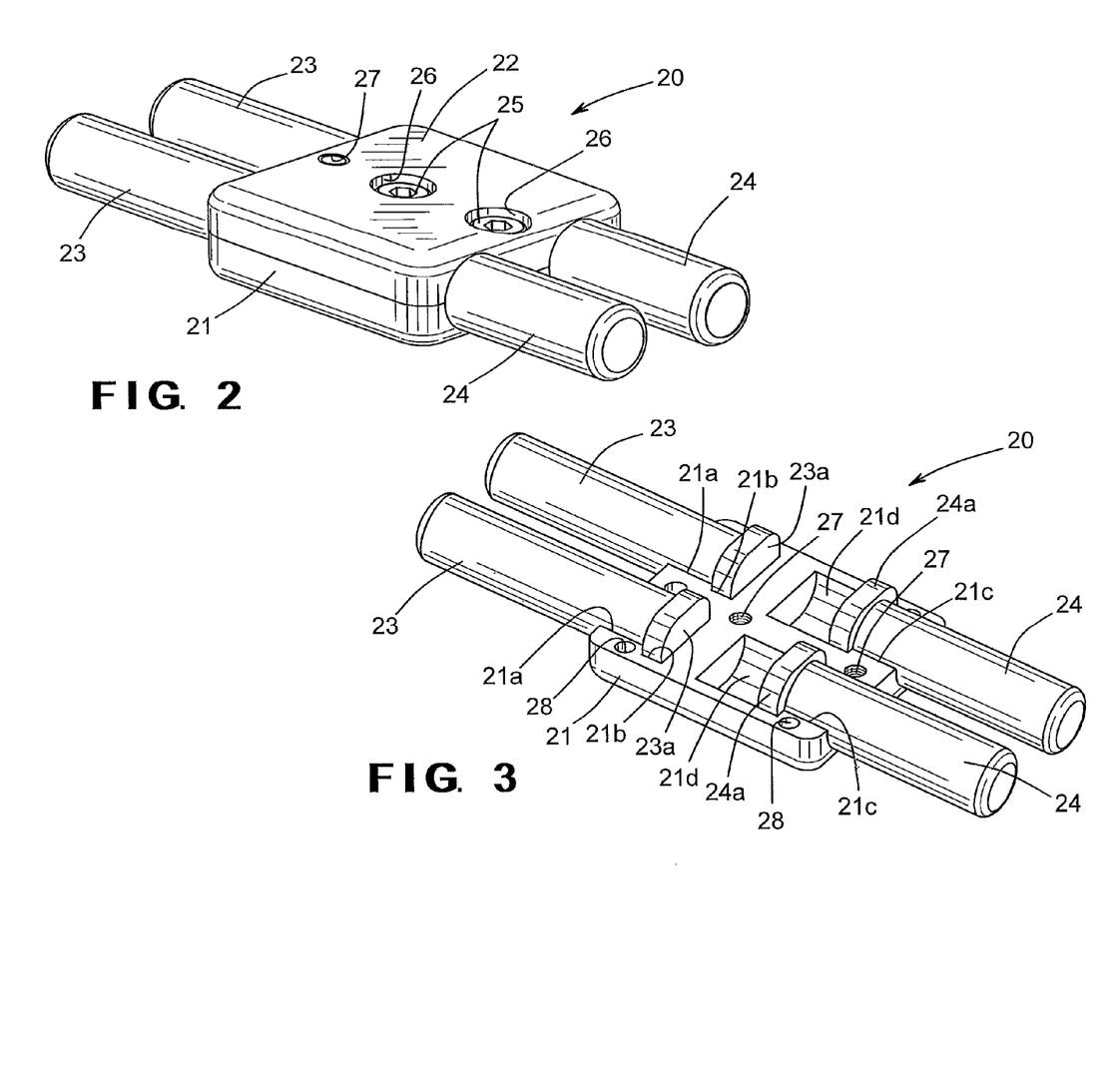
FIG. 2 is a perspective view of the first embodiment of the lateral fixation assembly illustrated in FIG. 1.
FIG. 3 is a perspective view of a portion of the first embodiment of the lateral fixation assembly illustrated in FIGS. 1 and 2.
Figure 4:
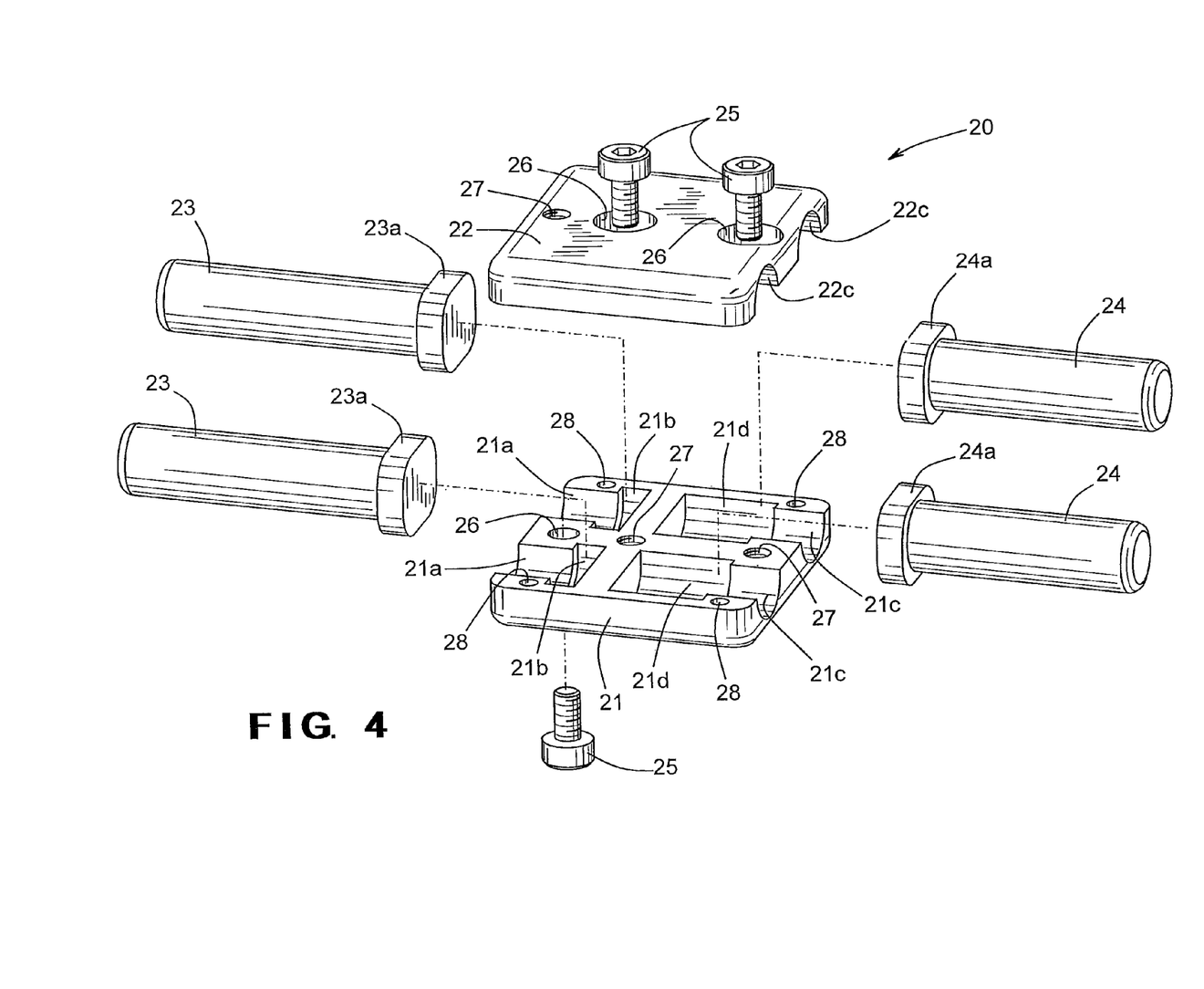
FIG. 4 is an exploded perspective view of the first embodiment of the lateral fixation assembly illustrated in FIGS. 1, 2, and 3.

The structure of the lateral fixation assembly 20 is illustrated in detail in FIGS. 2, 3, and 4. As shown therein, the lateral fixation assembly 20 includes a housing that, in the illustrated embodiment, is formed from a first housing portion 21 and a second housing portion 22. However, if desired, the housing of the lateral fixation assembly 20 may be formed from a greater or lesser number of pieces. In the illustrated embodiment, the first housing portion 21 is located adjacent to the vertebrae 10 and 11 when the lateral fixation assembly 20 is secured to each of the vertebrae 10 and 11, while the second housing portion 22 is located remote therefrom. However, the first and second housing portions 21 and 22 may be arranged in any desired relative locations.

The illustrated first housing portion 21 has a pair of first recesses 21a provided therein. It will be appreciated, however, that the first housing portion 21 may have a greater or lesser number of such first recesses 21a provided therein. In the illustrated embodiment, each of the first recesses 21a is generally semi-cylindrical in shape. However, the first recesses 21a may have any desired shape or combination of shapes. Each of the illustrated first recesses 21a has an enlarged region 21b, although such is not required. In the illustrated embodiment, each of the enlarged regions 21b is generally semi-square in shape. However, the enlarged regions 21b may have any desired shape or combination of shapes. The purposes for the first recesses 21a and the associated enlarged regions 21b will be explained below.

The illustrated first housing portion 21 also has a pair of second recesses 21c provided therein. It will be appreciated, however, that the first housing portion 21 may have a greater or lesser number of such second recesses 21c provided therein. In the illustrated embodiment, each of the second recesses 21c is generally semi-cylindrical in shape. However, the second recesses 21c may have any desired shape or combination of shapes. Each of the illustrated second recesses 21c has an enlarged region 21d, although such is not required. In the illustrated embodiment, each of the enlarged regions 21d is generally semi-square in shape. However, the enlarged regions 21d may have any desired shape or combination of shapes. The purposes for the second recesses 21c and the associated enlarged regions 21d will be explained below.

The illustrated second housing portion 22 may be shaped complementary to the first housing portion 21, having similar first recesses (not shown) having associated enlarged regions (not shown) and similar second recesses 22c having associated enlarged regions (not shown). When the first and second housing portions 21 and 22 are secured together as shown in FIGS. 1 and 2, the first recesses 21a and the associated enlarged regions 21b provided in the first housing portion 21 are aligned with the first recesses and the associated enlarged regions provided in the second housing portion 22. Similarly, the second recesses 21c and the associated enlarged regions 21d provided in the first housing portion 21 are aligned with the second recesses 22c and the associated enlarged regions provided in the second housing portion 22.

The lateral fixation assembly 20 also includes a pair of fixed rods 23. In the illustrated embodiment, each of the fixed rods 23 is shaped in correspondence with the shapes of the aligned first recesses 21a respectively provided in the first and second housing portions 21 and 22. However, the fixed rods 23 may have any desired shape or combination of shapes. Each of the illustrated fixed rods 23 also has an enlarged head portion 23a, although such is not required. In the illustrated embodiment, each of the enlarged head portions 23a is shaped in correspondence with the shapes of the aligned enlarged regions 21b respectively provided in the first and second housing portions 21 and 22, respectively. However, the enlarged head portions 23a may have any desired shape or combination of shapes.

The lateral fixation assembly 20 further includes a pair of movable rods 24. In the illustrated embodiment, each of the movable rods 24 is shaped in correspondence with the shapes of the aligned first recesses 21c and 22c respectively provided in the first and second housing portions 21 and 22. However, the movable rods 24 may have any desired shape or combination of shapes. Each of the illustrated movable rods 24 also has an enlarged head portion 24a, although such is not required. In the illustrated embodiment, each of the enlarged head portions 24a is shaped in correspondence with the shapes of the aligned enlarged regions 21d respectively provided in the first and second housing portions 21 and 22, respectively. However, the enlarged head portions 24a may have any desired shape or combination of shapes.

To assemble the lateral fixation assembly 20, the fixed rods 23 and their associated enlarged head portions 23a are respectively received within the first recesses 21a and their associated enlarged regions 21b provided on the first housing portion 21, as best shown in FIG. 3. Similarly, the movable rods 24 and their associated enlarged head portions 24a are respectively received within the second recesses 21c and their associated enlarged regions 21d provided on the first housing portion 21, as also best shown in FIG. 3. Then, the second housing portion 22 is secured to the first housing portion 21, as shown in FIGS. 1 and 2. This can be accomplished in any desired manner, such as by a plurality of threaded fasteners 25 extending through respective non-threaded apertures 26 into engagement with respective threaded apertures 27. If desired, one or more conventional dowel pins (not shown) may be disposed within dowel apertures 28 provided in both of the first and second housing portions 21 and 22 to securely retain such first and second housing portions 21 and 22 in alignment with one another.

As best shown in FIGS. 3 and 4, the axial lengths of the enlarged head portions 23a of the fixed rods 23 are approximately the same as the axial lengths of the enlarged regions 21b of the first recesses 21a. As a result, the fixed rods 23 are fixed in position relative to the first and second housing portions 21 and 22 and, therefore, cannot move axially relative thereto. However, the axial lengths of the enlarged head portions 24a of the movable rods 24 are somewhat smaller than the axial lengths of the enlarged regions 21d of the second recesses 21c. As a result, the movable rods 24 are not fixed in position relative to the first and second housing portions 21 and 22 and, therefore, can move axially relative thereto. The ability of the movable rods 24 to move axially relative to the first and second housing portions 21 and 22 accommodates a limited amount of compression of the defect region after the lateral fixation assembly 20 has been installed, as described above.

Figure 5:
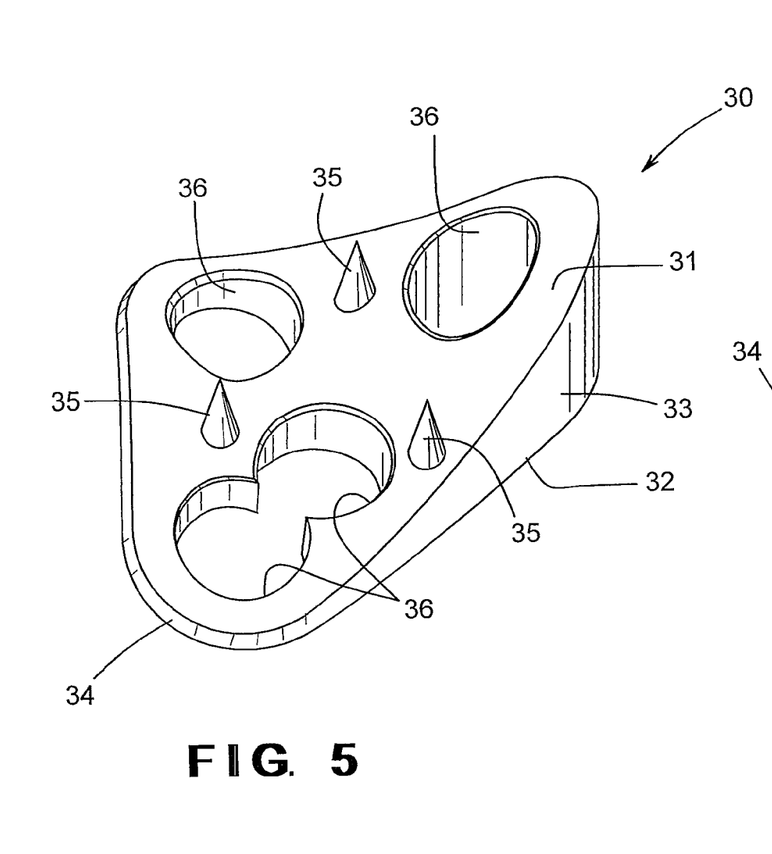
FIG. 5 is a perspective view of an inner side of a staple that can be used with the lateral fixation assembly of this invention.
Figure 6:
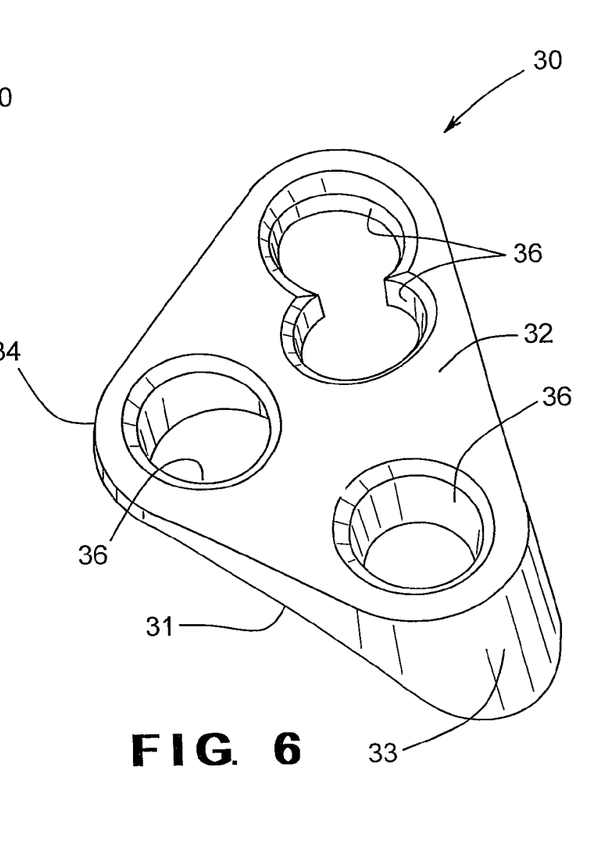
FIG. 6 is a perspective view of an outer side of the staple illustrated in FIG. 5.

Once the lateral fixation assembly 20 has been assembled, it can be secured to the vertebrae 10 and 11 by means of staples, indicated generally at 30. The structure of one of the staples 30 is illustrated in detail in FIGS. 5 and 6. As shown therein, the staple 30 includes a body having an inner surface 31 and an outer surface 32. As will be explained below, the thickness of the staple 30 (as defined by the distance between the inner surface 31 and the outer surface 32) varies throughout the body thereof from a relatively thicker portion 33 to a relatively thinner portion 34. The purpose for the varying thickness of the staple 30 will be explained below The staple 30 also includes one or more cleats 35 that are provided on the inner surface 31 thereof. The cleats 35 are configured for insertion into the vertebrae 10 and 11. In the illustrated embodiment, the cleats 35 have a generally triangular cross sectional shape that tapers to a point. However, the cleats 35 can have any other desired shape or combination of shapes. Although three cleats 35 are shown in the illustrated embodiment, it will be understood that the staple 30 may have a greater or lesser number of such cleats 35. Additionally, one or more apertures 36 are formed through the staple 30. Any desired number of such apertures 36 having any desired shape or combination of shapes may be provided in the staple 30. The staples 30 can be formed from titanium or any other desired material and may have any desired surface, finish, or coating. The staples 30 may be formed either from a single piece of material or from a plurality of pieces of material.

Referring back to FIG. 1, the staple 30 can be connected to the upper vertebra 10 by initially aligning the relatively thicker portion 33 of the staple 30 with the waist region 10d of the upper vertebra 10, and further by aligning the relatively thinner portion 34 of the staple 30 adjacent to the lower end plate 10b of the upper vertebra 10. As mentioned above, the waist region 10d of the upper vertebra 10 is concavely-shaped between the upper end plate 10a and the lower end plate 10b. By aligning the relatively thicker portion 33 of the staple 30 in the manner described above, the outer surface 32 of the staple 30 presents a generally flat and vertical surface that can be used to facilitate the securement of the fixed rods 23 of the lateral fixation device 20 thereto. Once the staple 30 has been aligned on the vertebra 10, it is moved toward the vertebra 10 such that the cleats 38 penetrate within the vertebra body 10c until the inner surface 31 of the staple 30 engages the surface of the waist region 10d of the vertebra 10. Similarly, the staple 30 can be connected to the lower vertebra 11 by aligning the relatively thicker portion 33 thereof with the waist region 11d of the lower vertebra 11, and by aligning the relatively thinner portion 34 of the staple 30 adjacent to the upper end plate 11a of the lower vertebra 11. Such alignment also presents a generally flat and vertical surface that can be used to facilitate the securement of the movable rods 24 of the lateral fixation device 20 thereto.

The staple 30 is preferably attached close to the lower end plate 10b of the vertebra 10 such that the triangular apical portion of the staple 30 (which is thicker than the rest thereof) sits generally flush with the waist 10d of the vertebra 10, thereby providing a stable surface. The inner surface 31 of the staple 30 is contoured such that it accommodates the transition from the end plate 10b to the waist region 10d and, therefore, is thicker toward the waist 10d. The thinner portion 34 of the staple 30 is placed close to the lower end plate 10b of the vertebra 10. The other staple 30 can be installed in a similar manner on the other vertebra 11.

In general, bone quality is better close to the end plates 10a and 10b of the vertebra 10 because there is more cortical bone in that region, as opposed to the cancellous bone in the region of the waist 10d of the vertebra 10. As a result, when the staple 30 and the vertebral anchors (described below) are placed close to the end plates 10a and 10b, stiffness and pull out strength are improved. In certain situations, when additional posterior fixation is anticipated as being necessary, it may be preferable to place both staples 30 close to the lower end plates 10b and 11b of the respective vertebra 10 and 11. With this arrangement, the screws placed though the staples 30 will be out of the path of vertebral anchors that are placed during subsequent posterior surgery.

When installed on the vertebrae 10 and 11, the staples 30 are adapted to engage and support one or more vertebral anchors, each indicated generally at 39. In the illustrated embodiment, the vertebral anchors 39 are conventional pedicle screws. Each of the illustrated pedicle screws 39 includes a head portion and a threaded shank portion. The shank portion of each pedicle screw 39 is initially threaded into engagement with one of the vertebrae 10 and 11. As shown in FIG. 1, the anchors 39 can be inserted through the apertures 36 of the staples 30 and into the vertebrae 10 and 12. The anchors 39 are inserted until the head portions thereof seat against the outer surfaces 32 of the staples 30. Thereafter, the head portion of each pedicle screw 39 is secured to one of the fixed and movable rods 23 and 24, respectively, of the lateral fixation assembly 20. In this or any other conventional manner, the lateral fixation assembly 20 can be secured to the vertebrae 10 and 11 for use.

Figure 7:
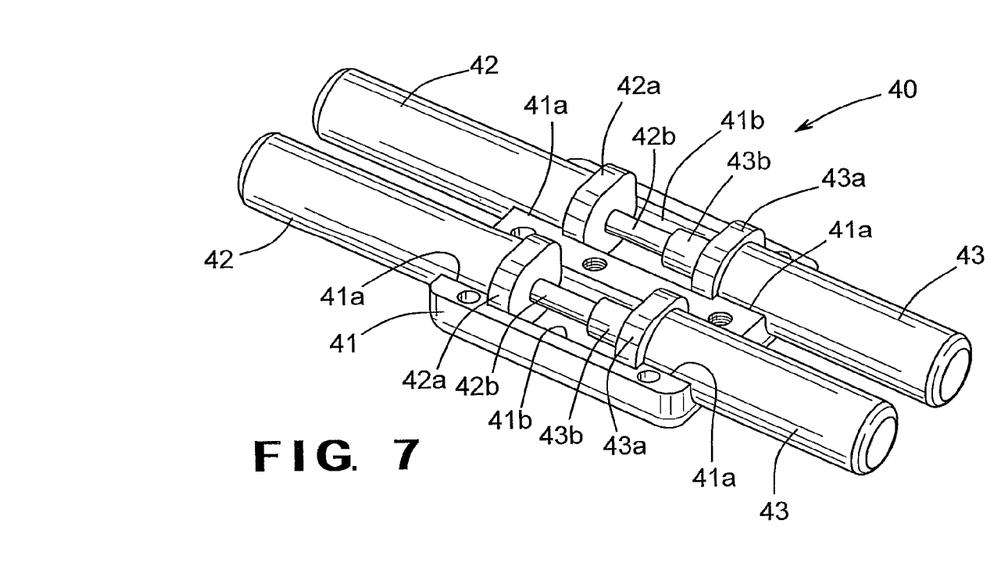
FIG. 7 is a perspective view similar to FIG. 3 of a second embodiment of a lateral fixation assembly in accordance with this invention.
Figure 8:
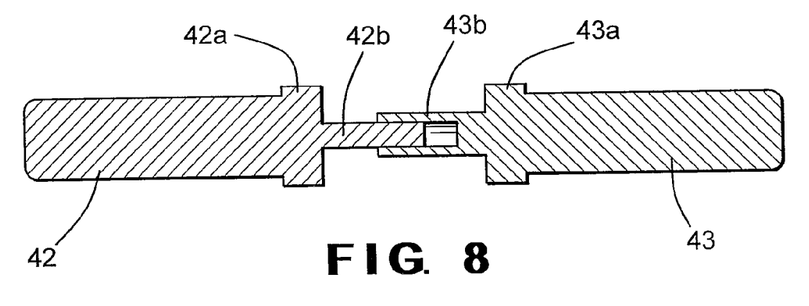
FIG. 8 is a sectional elevational view of a portion of the second embodiment of the lateral fixation assembly illustrated in FIG. 7.

FIGS. 7 and 8 illustrate portions of a second embodiment of a lateral fixation assembly, indicated generally at 40, in accordance with this invention. The second embodiment of the lateral fixation device 40 includes a housing that, in the illustrated embodiment, is formed from a first housing portion 41 and a second housing portion (not shown). The illustrated first housing portion 41 has a pair of first recesses 41a provided therein. If desired, the first housing portion 41 may have a greater or lesser number of such first recesses 41a provided therein. In the illustrated embodiment, each of the first recesses 41a is generally semi-cylindrical in shape. However, the first recesses 41a may have any desired shape or combination of shapes. Each of the illustrated first recesses 41a has an enlarged central region 41b, although such is not required. In the illustrated embodiment, each of the enlarged central regions 41b is generally semi-square in shape. However, the enlarged central regions 41b may have any desired shape or combination of shapes. The purposes for the first recesses 41a and the associated enlarged central regions 41b will be explained below.

The second embodiment of the lateral fixation assembly 40 also includes a first pair of rods 42. In the illustrated embodiment, each of the first pair of rods 42 is shaped in correspondence with the shapes of the aligned first recesses 41a respectively provided in the first and second housing portions 41. However, the first pair of rods 42 may have any desired shape or combination of shapes. Each of the illustrated first pair of rods 42 also has an enlarged head portion 42a and an axially extending journal portion 42b, although such is not required. In the illustrated embodiment, each of the enlarged head portions 42a is shaped in correspondence with the shapes of the aligned enlarged central regions 41b respectively provided in the first and second housing portions 41, respectively. However, the enlarged head portions 42a may have any desired shape or combination of shapes. The illustrated journal portions 42b are cylindrical in shape, although such is not required.

The second embodiment of the lateral fixation assembly 40 further includes a second pair of rods 43. In the illustrated embodiment, each of the second pair of rods 43 is shaped in correspondence with the shapes of the aligned first recesses 41a respectively provided in the first and second housing portions 41. However, the second pair of rods 43 may have any desired shape or combination of shapes. Each of the illustrated second pair of rods 43 also has an enlarged head portion 43a and an axially extending receiving portion 43b, although such is not required. In the illustrated embodiment, each of the enlarged head portions 43a is shaped in correspondence with the shapes of the aligned enlarged regions 41b respectively provided in the first and second housing portions 41, respectively. However, the enlarged head portions 43a may have any desired shape or combination of shapes. The illustrated receiving portions 43b have bores provided therein that are cylindrical in shape, although such is not required.

To assemble the second embodiment of the lateral fixation assembly 40, the journal portions 42b of the first rods 42 are inserted axially within the bores provided in the receiving portions 43b of the second rods 43, as best shown in FIG. 8. Then, the assembled first and second rods 42 and 43 (along with their associated enlarged head portions 42a and 43a) are respectively disposed within the first recesses 41a and their associated enlarged regions 41b provided on the first housing portion 41, as shown in FIG. 7. Thereafter, the second housing portion (not shown) is secured to the first housing portion 41 as described above. When so assembled, the first and second rods 42 and 43 are journaled on one another for axial movement relative to one another and relative to the housing of the second embodiment of the lateral fixation assembly 40. If desired, one or more of the first and second rods 42 and 43 can be fixed in position relative to the housing of the second embodiment of the lateral fixation assembly 40. This can be accomplished in the manner described above in connection with the embodiment of the invention illustrated in FIGS. 1 through 4.

Figures 9, 10:
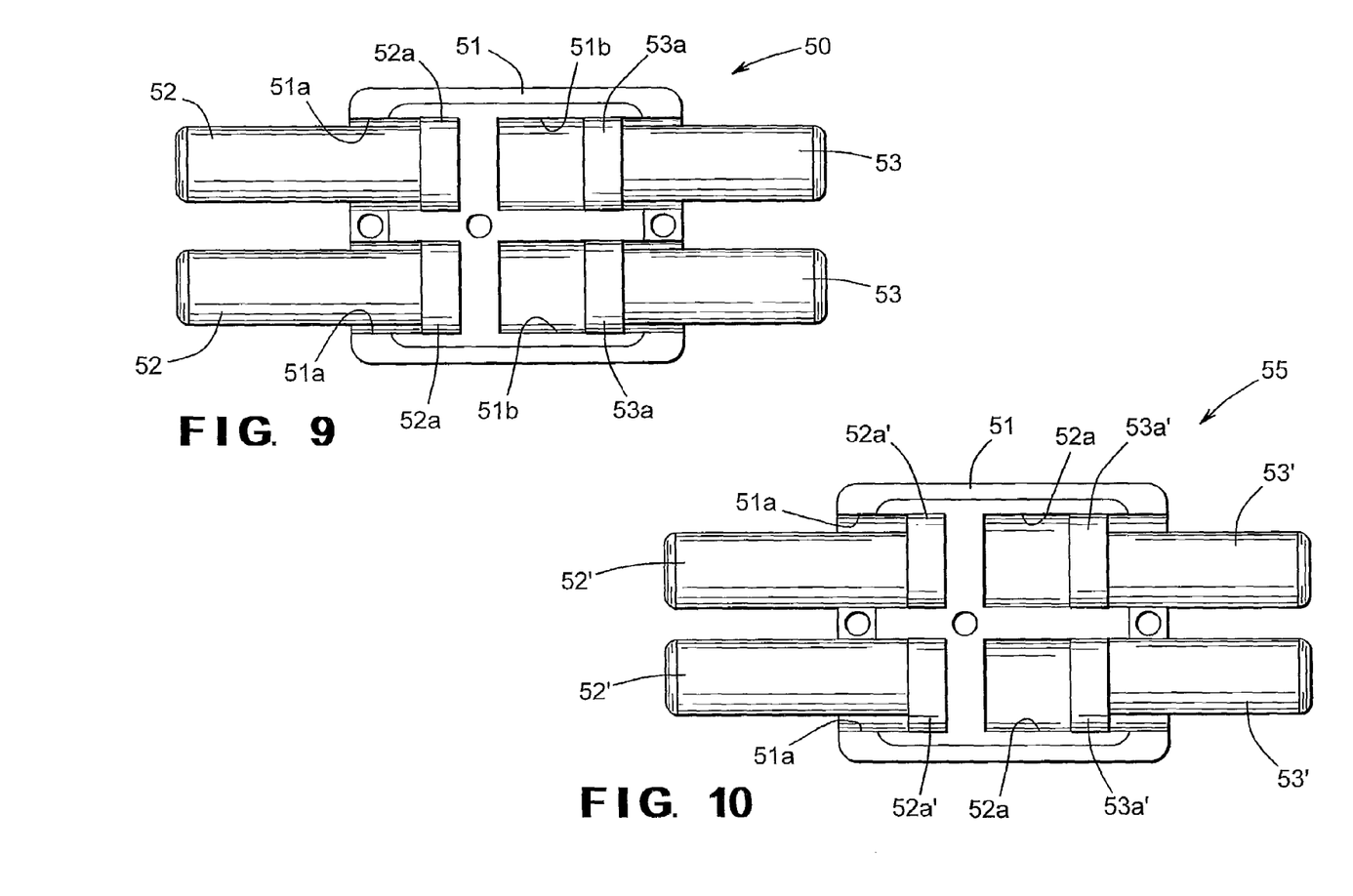
FIG. 9 is a top plan view of a third embodiment of a lateral fixation assembly in accordance with this invention having axially centered rods.
FIG. 10 is a top plan view of a fourth embodiment of a lateral fixation assembly in accordance with this invention having axially offset rods.

FIG. 9 illustrates a portion of a third embodiment of a lateral fixation assembly, indicated generally at 50, in accordance with this invention. The third embodiment of the lateral fixation device 50 includes a housing that, in the illustrated embodiment, is formed from a first housing portion 51 and a second housing portion (not shown). The illustrated first housing portion 51 has a pair of first recesses 51a provided therein. If desired, however, the first housing portion 51 may have a greater or lesser number of such first recesses 51a provided therein. In the illustrated embodiment, each of the first recesses 51a is generally semi-cylindrical in shape. However, the first recesses 51a may have any desired shape or combination of shapes. The illustrated first housing portion 51 also has a pair of second recesses 51b provided therein. As described above, the first housing portion 51 may have a greater or lesser number of such second recesses 51b provided therein. In the illustrated embodiment, each of the second recesses 51b is generally semi-cylindrical in shape. However, the second recesses 51b may have any desired shape or combination of shapes. The purposes for the first recesses 51a and the second recesses 51b will be explained below.

The third embodiment of the lateral fixation assembly 50 also includes a first pair of rods 52. In the illustrated embodiment, each of the first pair of rods 52 is shaped in correspondence with the shapes of the aligned first recesses 51a respectively provided in the first and second housing portions 51. However, the first pair of rods 52 may have any desired shape or combination of shapes. Each of the illustrated first pair of rods 52 also has an enlarged head portion 52a, although such is not required. In the illustrated embodiment, each of the enlarged head portions 52a is shaped in correspondence with the shapes of the first recesses 51a respectively provided in the first and second housing portions 51, respectively. However, the enlarged head portions 52a may have any desired shape or combination of shapes. In this third embodiment of the lateral fixation assembly 50, the enlarged head portions 52a are axially centered relative to the remainder of respective first rods 52.

The third embodiment of the lateral fixation assembly 50 further includes a second pair of rods 53. In the illustrated embodiment, each of the second pair of rods 53 is shaped in correspondence with the shapes of the aligned second recesses 51b respectively provided in the first and second housing portions 51. However, the second pair of rods 53 may have any desired shape or combination of shapes. Each of the illustrated second pair of rods 53 also has an enlarged head portion 53a, although such is not required. In the illustrated embodiment, each of the enlarged head portions 53a is shaped in correspondence with the shapes of the second recesses 51b respectively provided in the first and second housing portions 51, respectively. However, the enlarged head portions 53a may have any desired shape or combination of shapes. In this third embodiment of the lateral fixation assembly 50, the enlarged head portions 53a are axially centered relative to the remainder of respective second rods 53.

To assemble the third embodiment of the lateral fixation assembly 50, the first and second rods 52 and 53 (along with their associated enlarged head portions 52a and 53a) are respectively disposed within the first and second recesses 51a and 51b provided on the first housing portion 51, as shown in FIG. 9. Thereafter, the second housing portion (not shown) is secured to the first housing portion 51 as described above. When so assembled, the first and second rods 52 and 53 are supported for axial movement relative to the housing of the third embodiment of the lateral fixation assembly 50. If desired, one or more of the first and second rods 52 and 53 can be fixed in position relative to the housing of the third embodiment of the lateral fixation assembly 50. This can be accomplished in the manner described above in connection with the embodiment of the invention illustrated in FIGS. 1 through 4.

FIG. 10 illustrates a portion of a fourth embodiment of a lateral fixation assembly, indicated generally at 55, in accordance with this invention. The fourth embodiment of the lateral fixation device 55 is, in large measure, similar to the third embodiment 50 described above, and like reference numbers are used to indicate similar components. In the fourth embodiment of the lateral fixation assembly 55, the first and second housing portions 51 are the same as described above. However, the first pair of rods 52' have enlarged head portions 52a' that are axially offset relative to the remainder of respective first rods 52'. Similarly, the second pair of rods 53' have enlarged head portions 53a' that are axially offset relative to the remainder of respective second rods 53'.

The third and fourth embodiments of the lateral fixation device 50 and 55, respectively, illustrate how the distance between the adjacent ones of either (or both) of the first rods 52 and 52' and the second rods 53 and 53' can be quickly and easily adjusted to accommodate the dimensional characteristics of the vertebrae 10 and 11 that are being supported thereby. For example, in some instances, it may be desirable that such distance be relatively large. In those instances, the use of the first rods 52 having the axially centered enlarged head portions 52a would be desirable. In other instances, it may be desirable that such distance be relatively small. In those other instances, the use of the first rods 52' having the axially offset enlarged head portions 52a' would be desirable. It will be appreciated that any combination of the first rods 52 and 52' and the second rods 53 and 53' may be used as desired.

Figure 11:
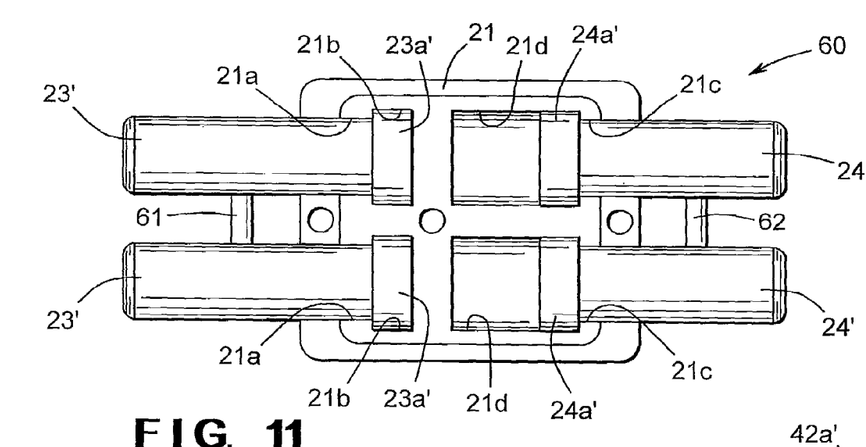
FIG. 11 is a top plan view of a fifth embodiment of a lateral fixation assembly in accordance with this invention having external stops.

FIG. 11 illustrates a portion of a fifth embodiment of a lateral fixation assembly, indicated generally at 60, in accordance with this invention. The fifth embodiment of the lateral fixation device 60 is, in large measure, similar to the first embodiment 20 described above, and like reference numbers are used to indicate similar components. In the fifth embodiment of the lateral fixation assembly 60, the first and second housing portions 21 are the same as described above. However, the pair of fixed rods 23' have a first external support rod 61 extending transversely therebetween. Similarly, the pair of movable rods 24' have a second external support rod 62 extending transversely therebetween. The support rods 61 and 62 provide increased support between the fixed rods 23' and the movable rods 24', respectively, and minimize any undesirable flexing thereof. Additionally, the support rods 61 and 62 function as external stops to limit the movements of the fixed rods 23' and the movable rods 24' inwardly toward one another. Although the illustrated support rods 61 and 62 are provided on both of the fixed rods 23' and the movable rods 24' in FIG. 11, it will be appreciated that this invention may be practiced with either only the first support rod 61 extending between the fixed rods 23' or only the second support rod 62 extending between the movable rods 24' as desired.

Figure 12:
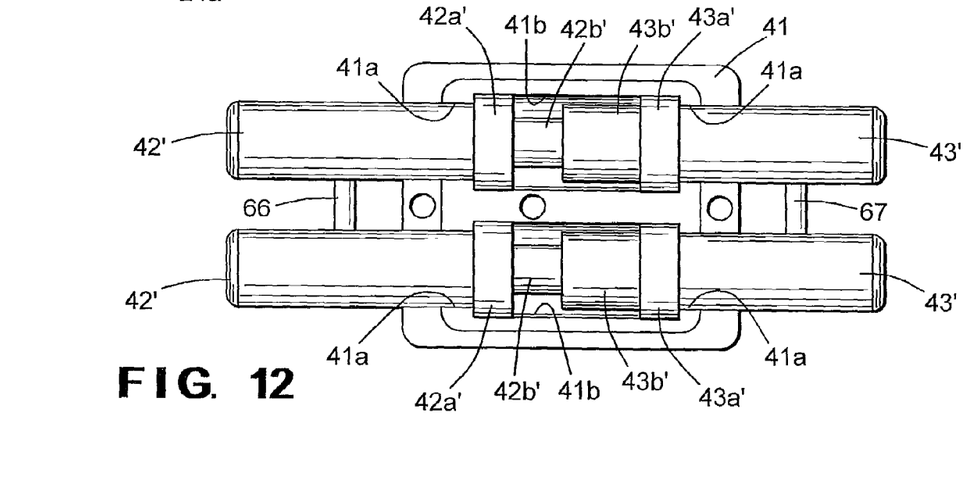
FIG. 12 is a top plan view of a sixth embodiment of a lateral fixation assembly in accordance with this invention having external stops.

FIG. 12 illustrates a portion of a sixth embodiment of a lateral fixation assembly, indicated generally at 65, in accordance with this invention. The sixth embodiment of the lateral fixation device 65 is, in large measure, similar to the second embodiment 40 described above, and like reference numbers are used to indicate similar components. In the sixth embodiment of the lateral fixation device 65, the first and second housing portions 41 are the same as described above. However, the first pair of rods 42' have a first external support rod 66 extending transversely therebetween. Similarly, the second pair of rods 43' have a second external support rod 67 extending transversely therebetween. The support rods 66 and 67 can be provided in the same manner and perform the same function as described above in connection with the support rods 61 and 62.

Figure 13:
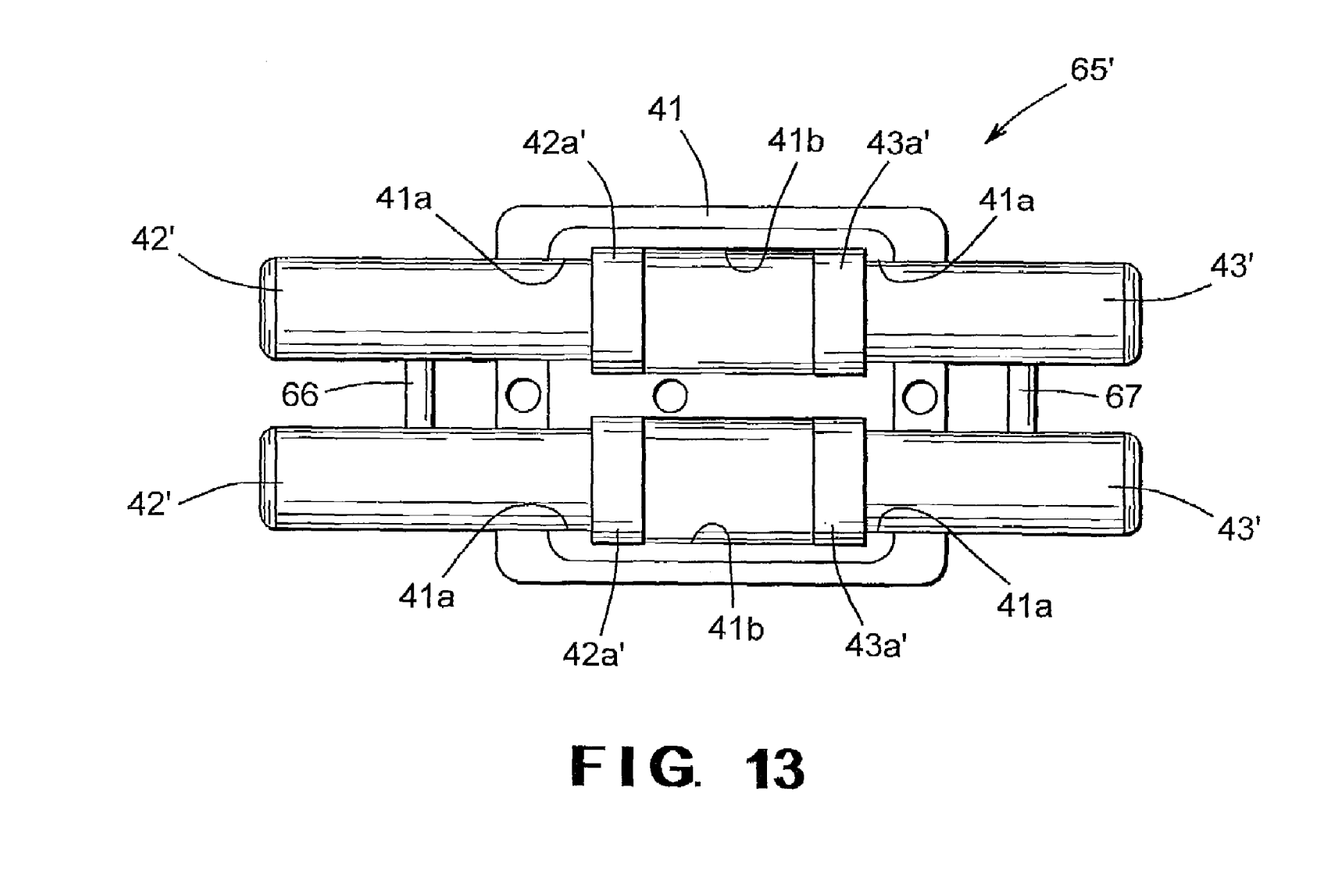
FIG. 13 is a top plan view of a seventh embodiment of a lateral fixation assembly in accordance with this invention having external stops.

FIG. 13 illustrates a portion of a seventh embodiment of a lateral fixation assembly, indicated generally at 65', in accordance with this invention. The seventh embodiment of the lateral fixation device 65' is, in large measure, similar to the sixth embodiment 65 described above, and like reference numbers are used to indicate similar components. In the seventh embodiment of the lateral fixation device 65', the journal portions 42b' and the receiving portions 43b' have been omitted from the rods 42 and 43, respectively. Otherwise, the seventh embodiment of the lateral fixation device 65' is the same as the sixth embodiment 65 described above.

Figures 14, 15:
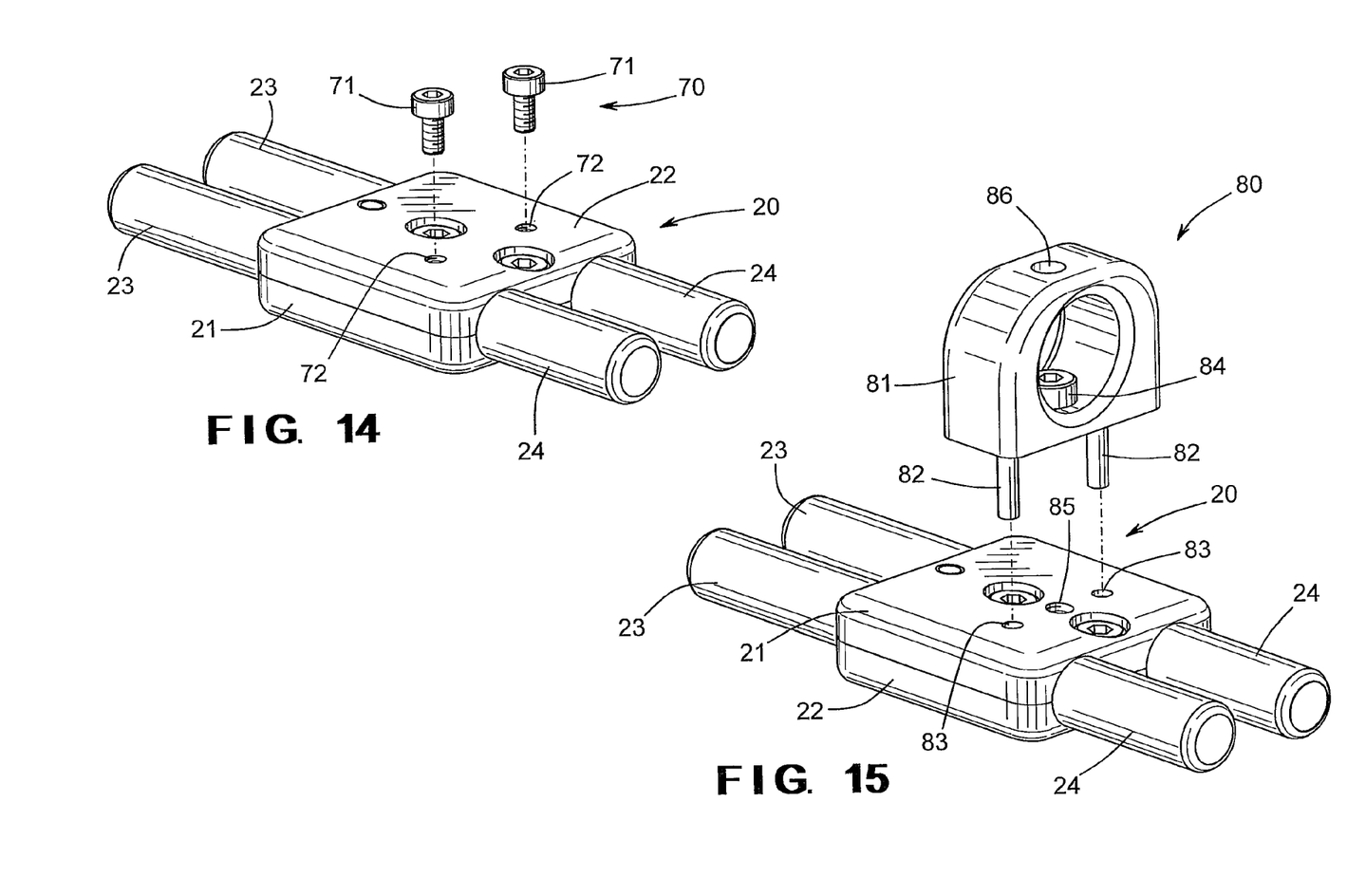
FIG. 14 is a perspective view of a first embodiment of a temporary blocking device that can be used to facilitate the installation of the lateral fixation assembly of this invention.
FIG. 15 is a perspective view of a second embodiment of a temporary blocking device that can be used to facilitate the installation of the lateral fixation assembly of this invention.

FIG. 14 illustrates a first embodiment of a temporary blocking device, indicated generally at 70, that can be used to facilitate the installation of the lateral fixation assembly of this invention on the vertebrae 10 and 11. Although the first embodiment of the temporary blocking device 70 will be described and illustrated in the context of the first embodiment of the lateral fixation assembly 20 of this invention, it will be appreciated that the first embodiment of the temporary blocking device 70 can be used in conjunction with any of the lateral fixation assemblies described and illustrated herein or with any other lateral fixation assembly having movable rods.

The first embodiment of the temporary blocking device 70 includes a pair of threaded fasteners 71 that are threaded into respective threaded apertures 72 formed through the second housing portion 22 of the lateral fixation assembly 20. The threaded apertures 72 extend through the second housing portion 22 of the lateral fixation assembly 20 into the enlarged regions 21d of the second recesses 21c, where the enlarged head portions 24a of the movable rods 24 are located. When the threaded fasteners 71 are so positioned, the inner ends thereof engage the enlarged head portions 24a of the movable rods 24, thereby preventing them from moving relative to the housing of the lateral fixation assembly 20. The threaded fasteners 71 of the first embodiment of the temporary blocking device 70 can be installed on the lateral fixation assembly 20 prior to installation on the vertebrae 10 and 11 to prevent any undesired movement of the movable rods 24 until after such installation has been completed. Once the installation of the lateral fixation assembly 20 has been completed, the threaded fasteners 71 of the first embodiment of the temporary blocking device 70 can be removed from the lateral fixation assembly 20 to allow movement of the movable rods 24 relative to the first and second housing portions 21 and 22 as described above.

FIG. 15 illustrates a second embodiment of a temporary blocking device, indicated generally at 80, that can be used to facilitate the installation of the lateral fixation assembly of this invention. Although the second embodiment of the temporary blocking device 80 will be described and illustrated in the context of the first embodiment of the lateral fixation assembly 20 of this invention, it will be appreciated that the second embodiment of the temporary blocking device 80 can be used in conjunction with any of the lateral fixation assemblies described and illustrated herein or with any other lateral fixation assembly having movable rods.

The second embodiment of the temporary blocking device 80 includes a body 81 having a pair of stops 82 extending therefrom. When the second embodiment of the temporary blocking device 80 is installed on the lateral fixation assembly 20, the stops 82 extend through respective apertures 83 formed through the second housing portion 22 of the lateral fixation assembly 20 and into the enlarged regions 21d of the second recesses 21c, where the enlarged head portions 24a of the movable rods 24 are located. When the stops 82 are so positioned, the inner ends thereof engage the enlarged head portions 24a of the movable rods 24, thereby preventing them from moving relative to the housing of the lateral fixation assembly 20.

The second embodiment of the temporary blocking device 80 can be installed on the lateral fixation assembly 20 prior to installation on the vertebrae 10 and 11 to prevent any undesired movement of the movable rods 24 until after such installation has been completed. To accomplish this, a threaded retaining fastener 84 can extend into engagement with a threaded aperture 85 provided in the second housing portion 22. If desired, an aperture 86 can be formed through a portion of the body 81 of the second embodiment of the temporary blocking device 80 to facilitate the installation and removal of the threaded retaining fastener 84. However, it will be appreciated that the second embodiment of the temporary blocking device 80 can be installed on the lateral fixation assembly 20 using any desired retaining structure. Once the installation of the lateral fixation assembly 20 has been completed, the second embodiment of the temporary blocking device 80 can be removed from the lateral fixation assembly 20 to allow movement of the movable rods 24 relative to the first and second housing portions 21 and 22 as described above.

In practice, the lateral fixation assembly 20 of this invention is installed following a corpectomy or other surgical procedure and the installation of the replacement structure 12 between the lower end plate 10b of the upper vertebra 10 and the upper end plate 11a of the lower vertebra 11. This is done by initially positioning the staples 30 on the vertebrae 10 and 11 and causing the cleats 35 to penetrate into such vertebrae 10 and 11. As a result, the staples 30 are secured to the vertebrae 10 and 11. Then, one or more of the pedicle screws 39 are inserted through the apertures 36 formed in the staples 30 and driven into the vertebrae 10 and 11 in a known manner. Next, the fixed rods 23 and the movable rods 24 of the lateral fixation assembly 20 are secured to the head portions of the pedicle screws 39 in a known manner. During this securement of the lateral fixation assembly 20 to the head portions of the pedicle screws 39, the temporary blocking device 70 or 80 may be installed on the lateral fixation assembly 20 to prevent any undesired relative movement of the movable rods 24. Lastly, however, after the lateral fixation assembly 20 has been secured to the head portions of the pedicle screws 39, the temporary blocking device 70 or 80 is removed from the lateral fixation assembly 20 to allow relative movement of the movable rods 24, as described above.

The principle and mode of operation of this invention have been explained and illustrated in its preferred embodiments. However, it must be understood that this invention may be practiced otherwise than as specifically explained and illustrated without departing from its spirit or scope.

What is claimed is:

1. A lateral fixation assembly for engaging vertebrae in a spinal column comprising:
a housing;
a first rod supported on the housing and adapted to be secured to a first vertebra in a spinal column, the first rod being fixed in position relative to the housing; and
a second rod supported on the housing and adapted to be secured to a second vertebra in a spinal column, the second rod being freely movable relative to the housing without the use of a tool and after engaging vertebrae in a spinal column.

2. The lateral fixation assembly defined in claim 1 wherein a plurality of first rods is supported on the housing, each of the first rods being fixed in position relative to the housing and wherein a plurality of second rods is supported on the housing, each of the second rods being movable relative to the housing.

3. The lateral fixation assembly defined in claim 1 wherein the housing has first and second recesses formed therein, and wherein the first rod is received within the first recess and the second rod is received within the second recess.

4. The lateral fixation assembly defined in claim 3 wherein the first rod has an enlarged head portion, and wherein the first recess has an enlarged region that receives the enlarged head portion of the first rod.

5. The lateral fixation assembly defined in claim 4 wherein the size of the enlarged head portion of the first rod is approximately the same as the size of the enlarged region of the first recess.

6. The lateral fixation assembly defined in claim 4 wherein the second rod has an enlarged head portion, and wherein the second recess has an enlarged region that receives the enlarged head portion of the second rod.

7. The lateral fixation assembly defined in claim 6 wherein the size of the enlarged head portion of the second rod is smaller than the size of the enlarged region of the second recess.

8. The lateral fixation assembly defined in claim 1 wherein the first and second rods are journaled on one another.

9. The lateral fixation assembly defined in claim 8 wherein the first rod has a journal portion provided therein, and wherein the second rod has a receiving portion provided therein that receives the journal of the first rod.

10. The lateral fixation assembly defined in claim 1 wherein the first rod has an enlarged head portion that is axially centered on the first rod.

11. The lateral fixation assembly defined in claim 10 wherein the first rod has an enlarged head portion that is axially centered on the first rod, and wherein the second rod has an enlarged head portion that is axially centered on the second rod.

12. The lateral fixation assembly defined in claim 1 wherein the first rod has an enlarged head portion that is axially offset on the first rod.

13. The lateral fixation assembly defined in claim 12 wherein the first rod has an enlarged head portion that is axially offset on the first rod, and wherein the second rod has an enlarged head portion that is axially offset on the second rod.

14. The lateral fixation assembly defined in claim 1 wherein a pair of first rods is supported on the housing, and wherein a first support rod extends transversely between the pair of first rods.

15. The lateral fixation assembly defined in claim 14 wherein a pair of second rods is supported on the housing, and wherein a second support rod extends transversely between the pair of second rods.

16. The lateral fixation assembly defined in claim 1 further including a temporary blocking device secured to the housing that prevents the second rod from moving relative to the housing.

17. The lateral fixation assembly defined in claim 16 wherein the temporary blocking device includes at least one threaded fastener that extends into a recess that receives the second rod.

18. The lateral fixation assembly defined in claim 16 wherein the temporary blocking device includes a body having a stop extending therefrom that extends into a recess that receives the second rod.

* * * * *